United States Patent [19]

Giudicelli et al.

[11] 4,010,161
[45] Mar. 1, 1977

[54] PIPERAZINOETHYL-N-(2,3-DIMETHYL-5-OXO-1-PHENYL-3Δ-PYRAZOLIN-4-YL)CARBAMATES

[75] Inventors: Don Pierre René Lucien Giudicelli, Fontenay-sous-Bois; Henry Najer; Bogdan Iliesco-Branceni, both of Paris; Philippe Michel Jacques Manoury, L'Hay-les-Roses; Jean Louis Christian Binet, Ballainvillers, all of France

[73] Assignee: Synthelabo, Paris, France

[22] Filed: Dec. 20, 1974

[21] Appl. No.: 534,792

[30] Foreign Application Priority Data

Dec. 21, 1973 France .............................. 73.45925

[52] U.S. Cl. .................... 260/268 PH; 260/293.7; 260/310 A; 424/250
[51] Int. Cl.² .......................... C07D 403/12
[58] Field of Search ... 260/268 H, 268 PH, 247.2 B, 260/310 A, 293.7; 424/250

[56] References Cited

UNITED STATES PATENTS 3,320,253  5/1967  Muhle et al. .................. 260/310 A

OTHER PUBLICATIONS

Mattalia et al., C. A. vol. 61, pp. 13288–13299, (1964).

Primary Examiner—Donald G. Daus
Assistant Examiner—Jose Tovar
Attorney, Agent, or Firm—Armstrong, Nikaido & Wegner

[57] ABSTRACT

Compounds of the formula:

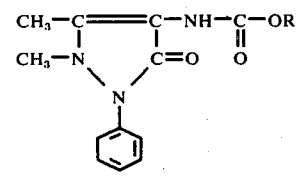

in which R represents a group of the formula:

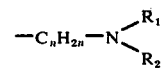

in which $n$ represents an integer of 1 to 5 and $R_1$ and $R_2$, which may be the same or different, each represents a hydrogen atom or a linear or branched, saturated or unsaturated aliphatic hydrocarbon group containing 1 to 5 carbon atoms, or $R_1$ and $R_2$, together with the nitrogen atom to which they are attached, form a heterocyclic ring having 5 to 7 ring members, which heterocyclic ring optionally contains a second heteroatom and/or one or more substituent groups, and their pharmaceutically acception acid addition salts, which compounds and salts are particularly suitable for use as analgesics.

5 Claims, No Drawings

PIPERAZINOETHYL-N-(2,3-DIMETHYL-5-OXO-1-PHENYL-3Δ-PYRAZOLIN-4-YL)CARBAMATES

The present invention relates to certain pyrazoline derivatives and their pharmaceutically acceptable acid addition salts, the preparation of such compounds and salts and pharmaceutical compositions containing them.

The present invention provides a compound of formula

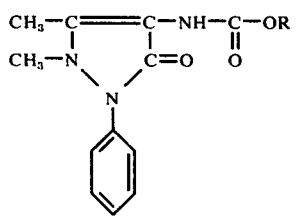

in which R represents a group of formula

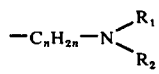

in which n represents an integer of 1 to 5, preferably 2 or 3, and $R_1$ and $R_2$, which may be the same or different, each represents a hydrogen atom or a linear or branched, saturated or unsaturated aliphatic hydrocarbon group containing 1 to 5 carbon atoms, or $R_1$ and $R_2$, together with the nitrogen atom to which they are attached, form a heterocyclic ring having 5 to 7 ring members, which heterocyclic ring optionally contains a second heteroatom (such as an oxygen, sulphur or nitrogen atom) and/or one or more substituent groups, or a pharmaceutically acceptable acid addition salt thereof. When

represents a heterocyclic group, it is preferably a piperidino group or a substituted piperazino group of formula

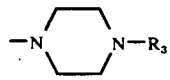

wherein $R_3$ represents a phenyl or benzyl group, the aromatic nucleus of which optionally bears one to three substituents which may be the same or different and are halogen atoms or alkyl, halogenoalkyl, alkylthio or halogenoalkylthio groups, the alkyl portions of which are linear or branched and contain 1 to 5 carbon atoms.

The invention also provides acid addition salts of the compounds of formula (I) with therapeutically acceptable mineral or organic acids such as hydrochloric acid, sulphuric acid, phosphoric acid, maleic acid, malic acid, citric acid, tartaric acid, oxalic acid and ascorbic acid.

The compounds of the invention and their salts are useful in human and veterinary medicine; they are especially effective as analgesics.

The compounds of the invention may be prepared by standard methods. A particularly suitable method involves a trans-esterification reaction as follows:

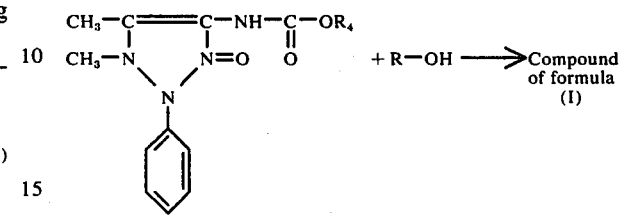

in which R is as defined above and $R_4$ represents a lower alkyl group, preferably a methyl or ethyl group.

The reaction is preferably carried out with the application of heat, under anhydrous conditions and in the presence of an inert organic solvent such as an aromatic hydrocarbon (for example benzene, toluene or xylene) and a trace of an alkali metal, for example sodium.

The acid addition salts of the compounds of formula (I) can be obtained in a conventional manner, for example by reacting approximately stoichiometric quantities of the compound of formula (I) and the acid in a polar solvent, such as an alcohol, an apolar solvent, such as an ether, or a mixture of such solvents.

The invention is illustrated by the following Examples.

EXAMPLE 1

2-(4-m-Chlorophenyl-piperazino)-ethyl N-(2,3-dimethyl-5-oxo-1-phenyl-3Δ-pyrazolin-4-yl)-carbamate and its tartrate. (n = 2;

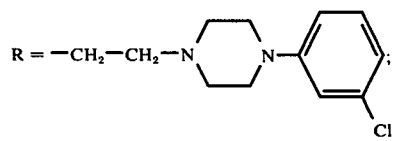

Code No. : SL B 207)

10 g. (0.041 mol) of 2-(4-m-chlorophenyl-piperazino)-ethanol, 11.5 g. (0.041 mol) of ethyl N-(2,3-dimethyl-5-oxo-1-phenyl-3Δ-pyrazolin-4-yl)-carbamate (prepared by the method of KNORR and STOLZ, Ann., 293, 66, (1896)) and 150 ml. of toluene are introduced into a distillation apparatus. The mixture is heated in order to drive off azeotropically the traces of water present in the reaction mixture. Whilst continuing to heat, 0.01 g. of sodium metal is added, and distillation is effected slowly in order to remove the ethanol formed in the trans-esterification reaction. After having heated for 4 hours, with two separate additions of sodium (0.010 g. in each case), the hot solution is filtered, and the filtrate is cooled and washed with water and then with 100 ml. of a 2N hydrochloric acid solution. The insoluble hydrochloride precipitates in the form of an oil which is decanted and the free base is liberated by stirring the oil with an aqueous solution of sodium carbonate. The basic product is extracted by means of chloroform, the chloroform solution is washed with water and dried and the solvent is driven off. The residual product solidifies, on trituration in ether. 7.95 g. (yield: 41.2%) of 2-(4-m-chlorophenyl-piperazino)-ethyl N-(2,3-dimethyl-5-oxo-1-phenyl-3Δ-pyrazolin-4-yl)-carbamate, which is slightly coloured and melts at 169° C., are thus obtained. When recrystallised from acetone, the product undergoes a change of crystalline form and then melts at 180°–190° C.

Analysis: $C_{24}H_{28}ClN_5O_3$ ; molecular weight: 469.975; Calculated % C 61.34 H 6.00 Cl 7.54; Found % 61.39 5.95 7.59.

The tartrate, which is very soluble in water, is prepared in almost quantitative yield by adding 0.1 mol of tartaric acid to a solution of 0.1 mol of the base in methanol. On adding ether, 2-(4-m-chlorophenyl-piperazino)-ethyl N-(2,3-dimethyl-5-oxo-1-phenyl-3Δ-pyrazolin-4-yl)-carbamate tartrate precipitates, and it is filtered off and dried.

Analysis: $C_{28}H_{34}ClN_5O_9$ ; molecular weight: 620.064 Calculated %, anhydrous: C 54.24 H 5.53 N 11.29 Cl 5.72 Calculated for 2.1% of $H_2O$ (KF) : 53.10 6.08 11.06 5.60 Found % : 53.40 5.76 10.72 5.54 53.49 5.70 5.50

EXAMPLE 2

2-(4-m-Trifluoromethylphenyl-piperazino)-ethyl N-(2,3-dimethyl-5-oxo-1-phenyl-3Δ-pyrazolin-4-yl)-carbamate.

(n = 2;

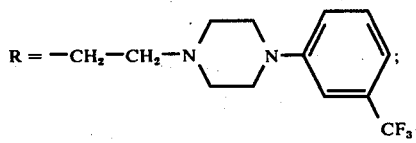

Code No.: SL B 102)

A mixture of 20 g. (0.073 mol) of ethyl N-(2,3-dimethyl5-oxo-1-phenyl-3Δ-pyrazolin-4-yl)-carbamate and 20 g. (0.073 mol) of 2-(4-m-trifluoromethylphenyl-piperazino)-ethanol is heated at 150°–160° C. for 2 hours. The reaction mixture is taken up in boiling toluene and is filtered in order to remove insoluble material. The organic solution is washed with water and is extracted with an aqueous solution of tartaric acid, a solution of sodium bicarbonate is added to the aqueous acid phase in order to liberate the base and extraction is effected using chloroform. The chloroform solution is washed with water, dried over anhydrous magnesium sulphate and filtered the solvent is evaporated from the filtrate and the oily residue is triturated in ether until it crystallises. 25 g. (yield: 68%) of 2-(4-m-trifluoromethyl-phenyl-piperazino)-ethyl N-(2,3-dimethyl-5-oxo-1-phenyl-3Δ-pyrazolin-4-yl)-carbamate, which melts at 175° C., are thus obtained.

Analysis: $C_{25}H_{28}F_3N_5O_3$ ; molecular weight: 503.528; Calculated % : C 59.63 H 5.61 N 13.91 F 11.32; Found % : 59.77 5.76 14.02 11.04 59.92 5.89 14.18.

EXAMPLE 3

2-(4-m-Trifluoromethylphenyl-piperazino)-ethyl N-(2,3-dimethyl-5-oxo-1-phenyl-3Δ-pyrazolin-4-yl)-carbamate hydrochloride.

(n = 2;

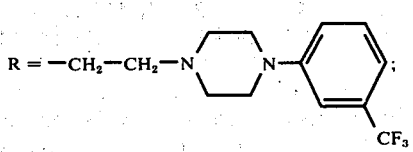

Code No.: SL B 186)

5 g. (0.01 mol) of 2-(4-m-trifluoromethylphenyl-piperazino)-ethyl N-(2,3-dimethyl-5-oxo-1-phenyl-3Δ-pyrazolin-4-yl)-carbamate, prepared as described in Example 2, are dissolved in acetone, and the calculated amount of a solution of hydrochloric acid in ether is added slowly. On adding a drop of water to the solution, the hydrochloride precipitates and it is filtered off and dried. 5.3 g. (yield: 98%) of 2-(4-m-trifluoromethylphenyl-piperazino)-ethyl N-(2,3-dimethyl-5-oxo-1-phenyl-3Δ-pyrazolin-4-yl)-carbamate hydrochloride are thus collected.

Analysis: $C_{25}H_{29}ClF_3N_5O_3$ ; molecular weight: 539.989 Calculated % C 55.61 H 5.41 N 12.97 Cl 6.56 Calculated for 1.8% 54.61 5.51 12.73 6.44 of $H_2O$ (KF) Found % 54.62 5.75 12.82 6.69 54.48 5.64 12.64 6.57

EXAMPLE 4

2-Dimethylamino-ethyl N-(2,3-dimethyl-5-oxo-1-phenyl-3Δ-pyrazolin-4-yl)-carbamate and its tartrate.

(n = 2;

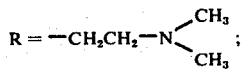

Code No.: SL B 215)

27.5 g. (0.1 mol) of ethyl N-(2,3-dimethyl-5-oxo-1-phenyl-3Δ-pyrazolin-4-yl)-carbamate, 22.2 g. (0.25 mol) of 2-dimethylamino-ethanol and 300 ml. of toluene are introduced into a distillation apparatus. By following the procedure described in Example 1, using 0.03 g. of sodium, added in several stages, the appearance of a precipitate is observed after heating for approximately 3 hours. The reaction mixture is cooled and filtered and 6.5 g. of N,N'-bis-(2,3-dimethyl-5-oxo-1-phenyl-3Δ-pyrazolin4-yl)-urea is removed. The base crystallises from the filtrate after it has been left to stand overnight. 11.2 g. (yield: 35.2%) of 2-dimethylamino-ethyl N-(2,3-dimethyl-5-oxo-1-phenyl3Δ-pyrazolin-4-yl)-carbamate, which is very soluble in water and melts at 136° C., are obtained.

Analysis: $C_{16}H_{22}N_4O_3$ ; molecular weight: 318.378; Calculated % C 60.36 H 6.96 N 17.60; Found % 60.50 7.21 17.37 60.32 7.27 17.43.

The tartrate is prepared in almost quantitative yield by adding 0.1 mol of tartaric acid to a solution of 0.1 mol of the base in acetone.

Analysis: $C_{20}H_{28}N_4O_9$ ; molecular weight: 469.468 Calculated %, anhydrous C 51.28 H 6.02 N 11.96 O 30.74 Calculated for 1.73% 50.39 6.11 11.75 31.75; of $H_2O$ (KF) Found % 50.28 6.29 11.69 31.72.

EXAMPLE 5

2-(4-m-Trifluoromethylthiophenyl-piperazino)-ethyl N-(2,3-dimethyl-5-oxo-1-phenyl-3Δ-pyrazolin-4-yl)-carbamate and its hydrochloride.

(n = 2;

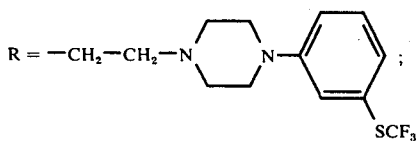

Code No.: SL B 208)

By following the procedure described in Example 1, but using 12.5 g. (0.045 mol) of ethyl N-(2,3-dimethyl-5-oxo-1-phenyl3Δ-pyrazolin-4-yl)-carbamate, 15.3 g. (0.05 mol) of 2-(4-m-trifluoromethylthiophenyl-piperazino)-ethanol, 200 ml. of toluene and 0.03 g. of sodium, the precipitation of N,N'-bis-(2,3-dimethyl-5-oxo-1-phenyl-3Δ-pyrazolin-4-yl)-urea is observed after heating for 4 hours. The reaction mixture is cooled and the insoluble material is filtered off. The toluene solution is washed with water and dried and the toluene is evaporated. When the residual oil is triturated in toluene, it solidifies. 8.4 g. of crude product are isolated and recrystallised from methanol. 6.85 g. (yield: 28.5%) of 2-(4-m-trifluoromethylthiophenyl-piperazino)-ethyl N-(2,3-dimethyl-5-oxo-1-phenyl-3Δ-pyrazolin-4-yl)-carbamate, which melts at 170° C., are thus obtained.

The monohydrochloride of this base is prepared by dissolving 5.35 g. (0.01 mol) of the base in chloroform and adding the calculated amount of a solution of hydrogen chloride in ether. The hydrochloride is filtered off and recrystallised from a mixture of acetone and chloroform. 5.05 g. (yield: 88.5%) of 2-(4-m-trifluoromethylthiophenyl-piperazino)-ethyl N-(2,3-dimethyl-5-oxo-1-phenyl-3Δ-pyrazolin-4-yl)-carbamate hydrochloride, which melts at 234° C., are collected.

Analysis: $C_{25}H_{29}ClF_3N_5O_3S$ ; molecular weight: 572.053 Calculated % C 52.49 H 5.11 N 12.24 Cl 6.20 Found % 52.34 5.19 12.10 6.14 52.43 5.19 6.17

EXAMPLE 6

2-(4-Phenyl-piperazino)-ethyl N-(2,3-dimethyl-5-oxo-1-phenyl-3Δ-pyrazolin-4-yl)-carbamate and its hydrochloride.

(n = 2;

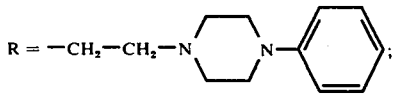

Code No.: SL B 197)

Using the procedure described in Example 1 but employing 20.7 g. (0.075 mol) of ethyl N-(2,3-dimethyl-5-oxo-1-phenyl-3Δ-pyrazolin-4-yl)-carbamate, 15.3 g. (0.075 mol) of 2-(4-phenylpiperazino)-ethanol, 200 ml. of toluene and 0.02 g. of sodium, the formation of degradation products is noted after heating for 3 hours. The boiling reaction mixture is filtered and the filtrate is cooled. A large amount of material crystallises. The crystals are filtered off, washed with ether and dissolved in chloroform and the organic solution is extracted with a 2N solution of hydrochloric acid. The aqueous acid phase is then rendered alkaline by means of a 2M solution of sodium carbonate, extraction is again effected using chloroform, the chloroform solution is washed and dried, the solvent is evaporated and the solid obtained is recrystallised from methanol. 10.3 g. (yield: 31.5%) of 2-(4-phenyl-piperazino)-ethyl N-(2,3-dimethyl-5-oxo-1-phenyl-3Δ-pyrazolin-4-yl)-carbamate, which melts at 186° C., are thus obtained.

Analysis: $C_{24}H_{29}N_5O_3$; molecular weight: 435.530 Determination of base: equivalent, calculated: 435.5 found 430

The monohydrochloride is formed by adding the stoichiometric amount of a solution of hydrochloric acid in ethanol to a solution of the base in methanol. On adding ether, the hydrochloride precipitates, and it is filtered off and washed with ether. 2-(4-Phenyl-piperazino)-ethyl N-(2,3-dimethyl-5-oxo-1-phenyl-3Δ-pyrazolin)-4-yl)-carbamate hydrochloride, which melts at 236° C, is thus obtained in a yield of 95%.

Analysis: $C_{24}H_{30}ClN_5O_3$; molecular weight: 471.991 Calculated % C 61.07 H 6.40 Cl 7.51 Found % 61.07 6.19 7.50 7.58

EXAMPLE 7

2-(4-p-Tolyl-piperazino)-ethyl N-(2,3-dimethyl-5-oxo-1-phenyl-3Δ-pyrazolin-4-yl)-carbamate and its hydrochloride.

(n = 2;

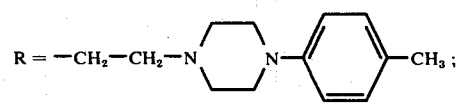

Code No.: SL B 209)

Following the procedure described in Example 1, 14.85 g. (0.054 mol) of ethyl N-(2,3-dimethyl-5-oxo-1-phenyl-3Δ-pyrazolin-4-yl)-carbamate, 11.9 g. (0.054 mol) of 2-(4-p-tolylpiperazino)-ethanol, 150 ml. of toluene and 0.03 g. of sodium are reacted together. After heating for 4 hours, the hot toluene solution is filtered. On cooling the filtrate, the basic product crystallises. It is filtered off, washed with ether and recrystallised from methanol. 11 g. (yield: 45.5%) of 2-(4-p-tolyl-piperazino)-ethyl N-(2,3-dimethyl-5-oxo-1-phenyl-3Δ-pyrazolin-4-yl)-carbamate, which melts at 200° C., are thus obtained.

The hydrochloride is prepared by adding the calculated amount of a solution of hydrochloric acid in ether to a solution of the base in tetrahydrofuran. 2-(4-p-Tolyl-piperazino)-ethyl N-(2,3-dimethyl-5-oxo-1-phenyl-3Δ-pyrazolin-4-yl)-carbamate hydrochloride is obtained in a yield of 90%. Its melting point is 220° C.

Analysis: $C_{25}H_{32}ClN_5O_3$ ; molecular weight: 486.018; Calculated % C 61.78 H 6.64 N 14.41 O 9.87 Cl 7.29; Found % 61.57 7.08 14.53 10.08 7.35.

EXAMPLE 8

2-Piperidino-ethyl N-(2,3-dimethyl-5-oxo-1-phenyl-3Δ-pyrazolin4-yl)-carbamate.

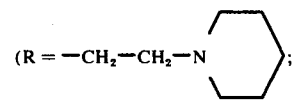

n = 2; Code No.: SL B 223)

A mixture of 13.7 g. (0.05 mol) of ethyl N-(2,3-dimethyl-5-oxo-1-phenyl-3Δ-pyrazolin-4-yl)-carbamate and 6.45 g. (0.05 mol) of 2-piperidino-ethanol is heated at 160° C., for 1 hour 30 minutes, and the reaction mixture is then chromatographed on a column of silica (15 g. of silica per 1 g. of the mixture). Elution is carried out using chloroform in order to remove the starting carbamate, then using acetone in order to remove the degradation products, and finally using a mixture of acetone and methanol (70/30) in order to obtain the desired product. The solvents are evaporated from the eluate and 6.9 g. (yield: 38.2%) of pure 2-piperidino-ethyl N-(2,3-dimethyl-5-oxo-1-phenyl-3Δ-pyrazolin-4-yl)-carbamate, which melts at 166° C., are obtained.

Analysis: $C_{19}H_{26}N_4O_3$; molecular weight: 358.444; Calculated % C 63.67 H 7.31 O 13.39 N 15.63; Found % 63.47 7.25 13.61 15.46.

The compounds of the invention were subjected to a series of pharmacological experiments which demonstrated their valuable properties, particularly their analgesic properties. The results, compared with those obtained using amidopyrine, chosen as the reference substance, are given in Table I.

Acute toxicity

The experiments were carried out on mice of the CD1 strain, of both sexes, and the 50% lethal doses were calculated graphically.

Analgesic effect

This effect was investigated in accordance with three conventional experimental procedures.

a. Effect against pain induced, in CD1 mice, by the intraperitoneal injection of acetic acid, using the method described by Koster and colleagues (Fed. Proc., 1959, 18, 42) and modified by Peterfalvi, Branceni and colleagues, (Med. Pharmacol. exp., 1966, 15, 254).

b. Test using a plate heated by acetone vapours, carried out on CD1 mice, using the technique of Eddy and Leimbach (J. Pharm. exp. Therap., 1953, 107, 386).

c. Tail-pinching test on CD1 mice, using the method of Haffner (Deutsch. med. Wachr., 1959, 55, 731).

The results obtained in the Koster test, which demonstrates analgesic effects of the peripheral type, show that the activity of most of the derivatives investigated is much greater than that of the reference substance.

In the heated plate test and the tail-pinching test, the compounds of the invention possess an activity which is often much greater than that of the reference substance, and is always at least of the same order of magnitude as that of the reference substance.

Anti-inflammatory effect

The test of oedema induced by carragenine in SJ rats, in accordance with the technique of Winter and colleagues, (Proc. Soc. exp. Biol. Med., 1962, III, 544) was used. The effects of the compounds of the invention are markedly lower than that of the reference product.

TABLE I

| Compounds | Acute toxicity Mice $LD_{50}$ mg/kg per os | Koster test Mice $AD_{50}(1)$ mg/kg per os | Heated plate Mice MAD(2) mg/kg per os at the end of | | Haffner test $AD_{50}(1)$ mg/kg per os | Inflammation induced by carragenine Rats $AD_{40}(3)$ mg/kg per os |
|---|---|---|---|---|---|---|
| | | | 30 mins. | 60 mins. | | |
| SLB-186 | 2,000 | 8 | 30 | 30 | 10 | 100 |
| SLB-197 | 400 | 30 | 150 | 100 | — | >100 |
| SLB-207 | 990 | 8 | 60 | 300 | 10 | 100 |
| SLB-208 | >1,000 | 17 | 300 | 100 | — | 76 |
| SLB-209 | 410 | 25 | 100 | 150 | 15 | >100 |
| SLB-215 | >1,000 | 60 | 300 | 300 | — | >100 |
| Aminopyrine | 850 | 40 | 175 | 275 | 75 | 50 |

(1)$AD_{50}$ = 50% active dose
(2)MAD = mean active dose
(3)$AD_{40}$ = 40% active dose These experimental data show that the compounds of the invention possess very marked analgesic properties, generally superior to those of amidopyrine.

They are also characterised by quite a marked separation between the analgesic properties and the anti-inflammatory properties; this separation is of great value for the specific treatment of algias.

Furthermore, several of the new derivatives possess a considerable therapeutic margin, because their toxicity is less than that of amidopyrine whilst their analgesic activity is much greater.

The compounds of formula (I) can thus be used in human and veterinary medicine for the treatment of various pain syndromes. Pharmaceutical compositions suitable for such use contain one or more compounds of formula (I) as active principle(s), in combination with any excipients which enable them to be administered orally, endorectally or parenterally. These pharmaceutical compositions can also contain other medicinal substances with which the compounds of formula (I) are pharmaceutically and therapeutically compatible.

For oral administration, the compositions can, for example, be in the form of tablets, dragees, gelatine-coated pills, capsules, cachets or potable solutions or suspensions. The unit dose of the compound of formula (I) suitably varies from 50 mg. to 500 mg., and suitable daily doses are 250 mg. to 2,000 mg. per day.

For rectal administration, suppositories containing 100 to 1,000 mg. of the compound of formula (I), which are administered to the patient at the rate of one to three per 24 hours, can be used.

For parenteral administration, injectable solutions buffered to the physiological pH can be used. In this case the unit dose is 50 to 500 mg. and the maximum daily dose is 1,000 mg.

We claim:

1. A compound which is 2-(4-m-chlorophenyl-piperazino)-ethyl N-(2,3-dimethyl-5-oxo-1-phenyl-3Δ -pyrazolin-4-yl)-carbamate or its tartrate.

2. A compound which is 2-(4-m-trifluoromethylphenyl-piperazino)-ethyl N-(2,3-dimethyl-5-oxo-1-phenyl-3Δ -pyrazolin-4-yl)-carbamate or its hydrochloride.

3. A compound which is 2-(4-m-trifluoromethylthiophenyl-piperazino)-ethyl N-(2,3-dimethyl-5-oxo-1-phenyl-3$\Delta$-pyrazolin-4-yl)-carbamate or its hydrochloride.

4. A compound which is 2-(4-phenyl-piperazino)-ethyl N-(2,3-dimethyl-5oxo-1-phenyl-3$\Delta$-pyrazolin-4-yl)-carbamate or its hydrochloride.

5. A compound which is 2-(4-p-tolyl-piperazino)-ethyl N-(2,3-dimethyl-5-oxo-1-phenyl-3$\Delta$-pyrazolin-4-yl)-carbamate or its hydrochloride.

* * * * *